United States Patent [19]

Millikan

[11] Plant 4,732

[45] Jun. 2, 1981

[54] RASPBERRY PLANT NAMED BABABERRY

[76] Inventor: Gertrude P. Millikan, 700 N. Stoneman, Alhambra, Calif. 91801

[21] Appl. No.: 104,565

[22] Filed: Dec. 17, 1979

[51] Int. Cl.[3] ..... A01H 5/03

[52] U.S. Cl. ..... Plt./46

[58] Field of Search ..... Plt./46

[56] References Cited

U.S. PATENT DOCUMENTS

P.P. 4,485 11/1979 Reiter ..... Plt./46

*Primary Examiner*—Robert E. Bagwill

[57] ABSTRACT

A vigorous everbearing red raspberry which thrives in warm, dry climates.

1 Drawing Figure

SUMMARY

This invention is a new and distinct variety of everbearing red raspberry which meets the long felt need for a raspberry variety which can withstand and flourish in hot dry climates such as that which exists in many parts of California.

DESCRIPTION OF THE PHOTOGRAPH

The photograph accompanying the application is an approximately life size view of the end of one stalk of the plant shows the leaves and ripening berries in varying degrees of maturity up to nearly ripe. Some of the stems have been turned so as to reveal the underside of some of the leaves. The size of the nearly ripe berries shown are typical of the size of the berries produced on the plant in both the spring and the fall crop.

DETAILED DESCRIPTION

Bababerry has proven to be an extremely strong and vigorous red raspberry, growing on strong stalks to a height of twelve feet when unattended, and bearing from four to eight strong, heavy bearing laterals when topped in the fashion usual to growers.

The canes carry somewhat soft prickles randomly on all sides of the canes at a rate of approximately 45 per inch of stem. The prickles achieve a maximum length of approximately one sixteenth inch. Emergent prickles are visible upon close inspection on the newest growth. The prickles, except in the newest 4 to 8 inches of new growth, are brown, their color being between Corinthian Purple and Neutral Red (Plate XXXVIII, Ridgway); when they have achieved their brown color the prickles are brown from their bases to their tips and contrast sharply with the bright green canes they are a part of. The emergent prickles on new growth carry the same bright green color as the new growth and gradually change to the brown color as they grow. The primocanes and new growth on floricanes are bright green, varying from Viridine Yellow to Cosse Green (Plate V, Ridgway). When exposed to hot direct sun, some of the bright green canes will change color on the side exposed to the direct sun, changing on that side to a color very similar to that of the prickles (between Corinthian Purple and Neutral Red, Plate XXXVIII, Ridgway). Many of the primocanes which are protected from the direct sun and some which are exposed to the direct sun will maintain their bright green color all over throughout the growing season except where the mature primocanes develop a brown bark the first foot or so above their bases. New growth on the floricanes also is bright green which varies from Viridine Yellow to Cosse Green (See Plate V, Ridgway). Like the primocanes, the bright green color may continue through the growing season on the new growth or may change to the brown color on the side exposed to heavy direct sun as with the primocanes. It produces two crops of berries, one in the spring and one in the fall. The berries are large, firm, of good quality, sweet and of excellent flavor. The leaves are sharply serrated, heavily veined and considerably corrugated. In comparisons with "Indian Summer", an existing variety of everbearing red raspberry, the corrugations of the older leaves of the new variety as contrasted with the flatter older leaves of Indian Summer is a distinguishing characteristic when the plants are not in berries.

Foliage is nearly all three foliate, but there are a few four foliate and five foliate leaves. The three leaflets are cordate. The terminal leaflet sometimes develops lobes, either single, or one on each side, the lobes being a little above midway between the base and the apex. On a few of the terminal leaves with lobes a lobe may nearly separate from the terminal leaflet which would create a four foliate leaf pattern if the separation of a lobe were complete. The leaves are markedly corrugated from their first formation through to their maturity. New leaves are Deed Dull Yellow Green (1) (Plate XXXII, Ridgway). Mature leaves are Varley's Green (Plate XVIII, Ridgway) with the obverse side being Asphodel Green (Plate XLI, Ridgway). Many of the leaves show no difference in color at the margins but other leaves, due to the effects of exposure to heavy direct sunlight, develop a brown color similar to that of the canes (Corinthian Purple to Neutral Red, Plate XXXVIII, Ridgway) along the margins of the leaves. The brown color does not disappear with maturity of the leaves. Bababerry adapts well to a wide variety of soil conditions and temperatures. It is easy to grow. It is extremely vigorous and is quite disease resistant. Tests taken against one of the best everbearing raspberry varieties grown in southern California, Indian Summer, show that the new variety produces berries which are, on the average, larger, sweeter, and juicier. The berries, to most of those who have compared, are of better flavor.

The new variety is of unknown parentage. The original raspberry plant of the new variety was discovered in cultivation on my property in Idyllwild, Calif., a mountain valley of approximately one mile altitude in Riverside County. The temperature there drops to 9° on occasion in winter. The summers are fairly warm, often reaching 90° maximums, and the humidity is relatively low. While the new variety was growing in Idyllwild I recognized it to be a particularly vigorous and productive raspberry, with large and delicious berries, but because of the cold winters and relatively mild summers which I believed were necessary for heavy raspberry production, I didn't recognize one of its most outstanding unique characteristics until I moved from Idyllwild in 1974. In 1974 I moved to Los Angeles County and moved the plants to a warm, dry area near Pasadena, to the residence of my children. In the five succeeding years the plants I moved have developed through asexual reproduction to over 1000 plants which have maintained the characteristics of the original plant of the new variety. Asexual reproduction has been made through cuttings and root runner division.

The second year the raspberries were growing in La Canada - Flintridge, (near Pasadena), I felt sure that what seemed in Idyllwild to be an unusually vigorous and delicious red raspberry was a unique new variety. The raspberry thrived in the hot dry climate of Los Angeles County and was a heavy producer. I then began testing the new raspberry on the advice of several horticulturists who were impressed with its possibilities. I decided to have it tested against what is often considered to be the best of the everbearing varieties grown in southern California since the new variety is an everbearing raspberry. The tests by horticulturists included tests by the Los Angeles County and State Arboretum in Arcadia, Calif., the Garden Editors of the Los Angeles Times and the Pasadena Star News, and by one of the large commercial nurseries in California. Tests were also made with individuals growing the plants in their home gardens under differing soil and climate conditions and with many lacking knowledge or experience in berry growing. The results were tabulated and recorded. In all cases where the plants had been consistently watered the results were outstanding. When comparisons were made in identical growing conditions, the berries on the new variety were larger, juicier, sweeter, of better flavor and firmer. The plants were less affected by heat.

I named the new variety "Bababerry".

VIGOR OF THE PLANT

I made many tests of my own to discover the vigor of the plant. I moved and divided the stock at the worst possible times, as well as when the plants were dormant, with equally good results. As is necessary with raspberry plants, I did not intend to allow the soil to become dry, but one group of plants was accidentally neglected as to irrigation and became dry for a number of days during a period when the temperature was in the 100° maximums, thus giving a particularly good test of heat resistance. With the resumption of water, the plants responded well and showed no permanent damage and with few exceptions the berries continued to ripen as before.

Tests for temperature tolerance were made by using the known low of 9° in the Idyllwild mountains and the known high of 110° in La Canada-Flintridge on Sept. 5, 1979. Days of high temperatures in September 1979 were followed by cooler weather and, in November by a sudden frost. This drop in temperature killed the figs on the fig trees and roses and marigolds in the garden, but caused no change in the appearance of the leaves or the remainder of the fall crop of ripening raspberries, most of which continued to ripen.

The plants were carefully watched for signs of disease or pests. No sign of disease has been noted. There are many gophers in the area and surprisingly they seem to cause no problem. Despite their many mounds near and among the plants, they have not killed any of them and have not caused any noticeable damage.

BERRIES

The berries are deep red when fully ripe, borne in large clusters of up to fifty berries on the laterals. They are to the size of a thimble, longer than wide. When ripe they remain firm and do not crumble, as do many varieties. They do not fall off the stems until much over ripe. They have a fairly long ripening period from the early to the late berries of a crop, the peak being in June for the Spring crop and October for the Fall crop. It is an exceptional berry plant for the home garden.

The fruit is borne in cymose clusters. The terminal cluster bears between five and twelve berries. Subterminal clusters oftentimes bear as many or more berries as the terminal cluster. There may be ten or more subterminal clusters. The color of the ripe fruit is Bordeaux (Plate XII, Ridgway). The berries are extremely large. The largest berries which are of a size which develops with considerable frequency (as contrasted with even larger berries which occur with little frequency) are approximately $\frac{7}{8}$ths inch in length and $\frac{5}{8}$ths inch in diameter at the widest point. The berries are elongated and most are somewhat cone or beehive shaped as shown in the photograph which was submitted with the application. Primary berries have from 52 to 68 drupelets. Drupelets have a plainly visible median depression and are not uniform in size. The receptacle first tapers outward from the stem and sepals and then inward in an arc to a point. The point is somewhat rounded. The berries pick easily but do not fall from the receptacle.

USE

The berries keep well when picked for eating, freeze well, and cook well for canning or preserving. They combine well with other fruits either for eating when fresh or for canning or for preserving.

I claim:

1. I claim a new and distinct variety of everbearing red raspberry which can withstand and thrive in the warm dry climate portions of California and other similar climates and which is unusually hardy and vigorous, disease resistant and a heavy producer of large crops of firm, large, sweet, juicy raspberries of deep red color and excellent flavor, substantially as herein shown and described and identified by characteristics described above.

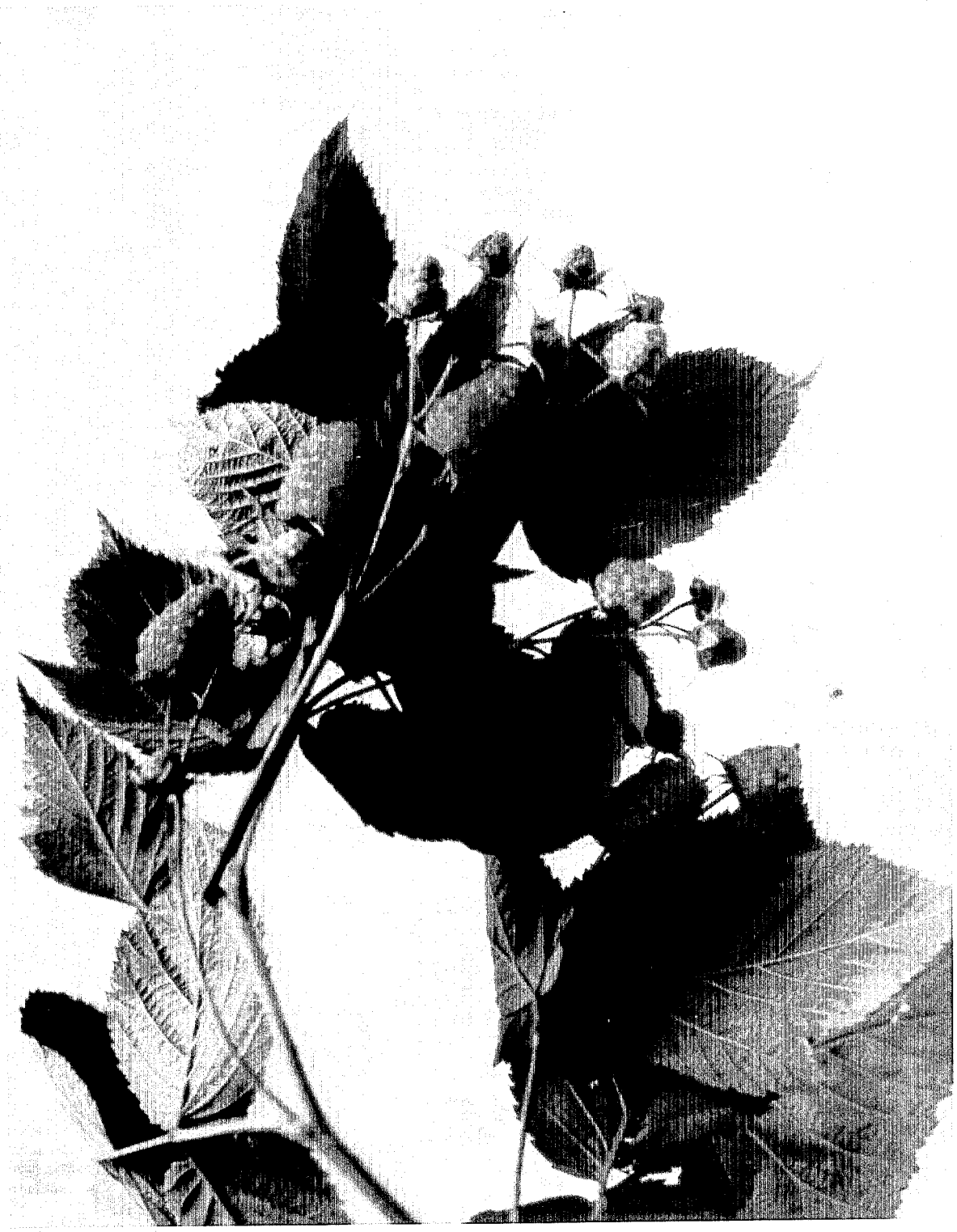

* * * * *